(12) United States Patent
'T Hooft et al.

(10) Patent No.: US 11,206,999 B2
(45) Date of Patent: Dec. 28, 2021

(54) FLEXIBLE INSTRUMENT CHANNEL INSERT FOR SCOPE WITH REAL-TIME POSITION TRACKING

(71) Applicant: KONINKLIJKE PHILIPS N.V., Eindhoven (NL)

(72) Inventors: Gert 'T Hooft, Eindhoven (NL); Adrien Emmanuel Desjardins, Waterloo, CA (US); Raymond Chan, San Diego, CA (US); Guy Shechter, Briarcliff Manor, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 721 days.

(21) Appl. No.: 16/003,147

(22) Filed: Jun. 8, 2018

(65) Prior Publication Data
US 2018/0303376 A1     Oct. 25, 2018

Related U.S. Application Data

(62) Division of application No. 13/521,579, filed as application No. PCT/IB2010/055607 on Dec. 6, 2010, now abandoned.

(Continued)

(51) Int. Cl.
*A61B 5/06*     (2006.01)
*A61B 1/00*     (2006.01)
(Continued)

(52) U.S. Cl.
CPC .............. *A61B 5/061* (2013.01); *A61B 1/005* (2013.01); *A61B 1/00082* (2013.01);
(Continued)

(58) Field of Classification Search
CPC ..... A61B 1/00082; A61B 1/005; A61B 1/018; A61B 2034/2061; A61B 5/061; A61B 5/1076; G01D 5/35383; G02B 6/022
See application file for complete search history.

(56) References Cited

U.S. PATENT DOCUMENTS 6,868,195 B2     3/2005  Fujita
7,930,065 B2     4/2011  Larkin et al.
(Continued)

FOREIGN PATENT DOCUMENTS

CN     101158734 A     4/2008
JP     2002200030 A    7/2002
(Continued)

*Primary Examiner* — Amelie R Davis

(57) ABSTRACT

An apparatus, system and method for determining a position of an instrument (100) includes a sheath (104) configured to fit within an instrument channel of a medical scope. An optical fiber (112) is disposed within the sheath and a plurality of sensors (106) is integrated in optical fiber. The sensors are configured to measure deflections and bending in the optical fiber. A fixing mechanism (140) is sized to fit within the instrument channel in a first state and fixes the sheath within the instrument channel in a second state such that the fixing mechanism anchors the sheath and the optical fiber so that the deflections and bending in the optical fiber are employed with a pre-procedural volumetric image to determine a position of the instrument.

8 Claims, 5 Drawing Sheets

Related U.S. Application Data

(60) Provisional application No. 61/294,849, filed on Jan. 14, 2010.

(51) Int. Cl.
*A61B 1/005* (2006.01)
*A61B 1/018* (2006.01)
*A61B 5/107* (2006.01)
*G01D 5/353* (2006.01)
*G02B 6/02* (2006.01)
*A61B 34/20* (2016.01)

(52) U.S. Cl.
CPC ............ *A61B 1/018* (2013.01); *A61B 5/1076* (2013.01); *G01D 5/35383* (2013.01); *A61B 2034/2061* (2016.02); *G02B 6/022* (2013.01)

(56) References Cited

U.S. PATENT DOCUMENTS

| | | |
|---|---|---|
| 2002/0041723 A1 | 4/2002 | Ronnekleiv et al. |
| 2004/0165810 A1 | 8/2004 | Fujita |
| 2005/0182295 A1* | 8/2005 | Soper ................. A61B 1/00172 600/117 |
| 2006/0013523 A1 | 1/2006 | Childlers et al. |
| 2007/0156019 A1 | 7/2007 | Larkin et al. |
| 2008/0091073 A1 | 4/2008 | Park |
| 2008/0130108 A1 | 6/2008 | Bayer et al. |
| 2008/0287963 A1 | 11/2008 | Rogers et al. |
| 2009/0123111 A1 | 5/2009 | Udd |

FOREIGN PATENT DOCUMENTS

| | | |
|---|---|---|
| JP | 2002306403 A | 10/2002 |
| JP | 2004121749 A | 4/2004 |
| WO | WO200133165 | 5/2001 |

* cited by examiner

FLEXIBLE INSTRUMENT CHANNEL INSERT FOR SCOPE WITH REAL-TIME POSITION TRACKING

CROSS-REFERENCE TO PRIOR APPLICATIONS

This application is a divisional of U.S. application Ser. No. 13/521,579, filed Jul. 11, 2012. which is a U.S. National Phase application under 35 U.S.C. § 371 of International Application Serial No. PCT/IB2010/055607, filed on Dec. 6, 2010, which claims the benefit of U.S. Patent Application No. 61/294,849, filed on Jan. 14, 2010. These applications are hereby incorporated by reference herein.

BACKGROUND

Technical Field

This disclosure relates to medical devices, and more particularly to medical devices employing fiber optic technology for position tracking during procedures.

Navigating a bronchoscope to a target in a bronchial tree of the lungs can be very challenging, even for experienced physicians. In the case of a suspected malignancy or other growth, a target is typically identified by computed tomography (CT), and as follow-up, a biopsy is performed via an instrument channel of a bronchoscope. However, with bronchoscopy, there is often a dearth of visual features for determining a direction to navigate at branch points and therefore physicians can get disoriented. The process of getting to the target can be very inefficient, which can result in increased procedure time or a tissue biopsy from an incorrect location.

A significant step forward for pulmonologists would be to have a robust method for correlating a position of the bronchoscope tip with a CT image volume. Different methods have been proposed to achieve this, and each has its disadvantages. One method includes electromagnetic (EM) navigation. In good cases, accuracy can be in the range of 1-2 mm, which is sufficient. This method involves a lengthy and complicated setup process in which EM sensors are positioned around the patient. Additionally, this method is sensitive to the presence of external fields which can significantly degrade accuracy. Another method includes registration of visual features observed with the bronchoscope with 3D fly-through reconstructions obtained from pre-procedurally-acquired 3D datasets. This method has the disadvantage that often there are insufficient visual cues to provide robust registration.

It would be advantageous to provide systems and methods where positioning and placement of medical devices is reliably performed.

SUMMARY

In accordance with the present principles, an apparatus, system and method for determining a position of an instrument are provided. A sheath is configured to fit within an instrument channel of a medical scope. An optical fiber or fibers are disposed within the sheath and a plurality of sensors is integrated in optical fiber(s). The sensors are configured to measure deflections and bending in the optical fiber. A fixing mechanism is sized to fit within the instrument channel in a first state and fixes the sheath within the instrument channel in a second state such that the fixing mechanism anchors the sheath and the optical fiber so that the deflections and bending in the optical fiber are employed to determine a position of the instrument.

A system for tracking of a portion of a medical device includes spatially distributed Fiber Bragg Gratings (FBGs) integrated on an optical fiber and disposed within a flexible insert, the flexible insert being positionable within an instrument channel of the medical device. An optical system is configured to deliver light to the FBGs and receive light from the FBGs such that deflections of the optical fiber are measured. A computer system includes a shape determination program configured to compute parameters related to the deflections of the optical fiber and determine a configuration of the flexible insert, and a map volume acquired from a pre-procedural scan such that based upon a comparison between the configuration of the flexible insert and the map volume a position of the medical device is determined.

A method for tracking of a portion of a medical device includes inserting a sheath into an instrument channel, the sheath including an optical fiber and a plurality of distributed sensors integrated with the optical fiber; anchoring the sheath within the instrument channel; determining a reference position within a patient using a pre-procedural volume of the patient, and determining a shape of the optical fiber using the sensors and correlating the shape with the pre-procedural volume to provide a location of the portion of the medical device.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
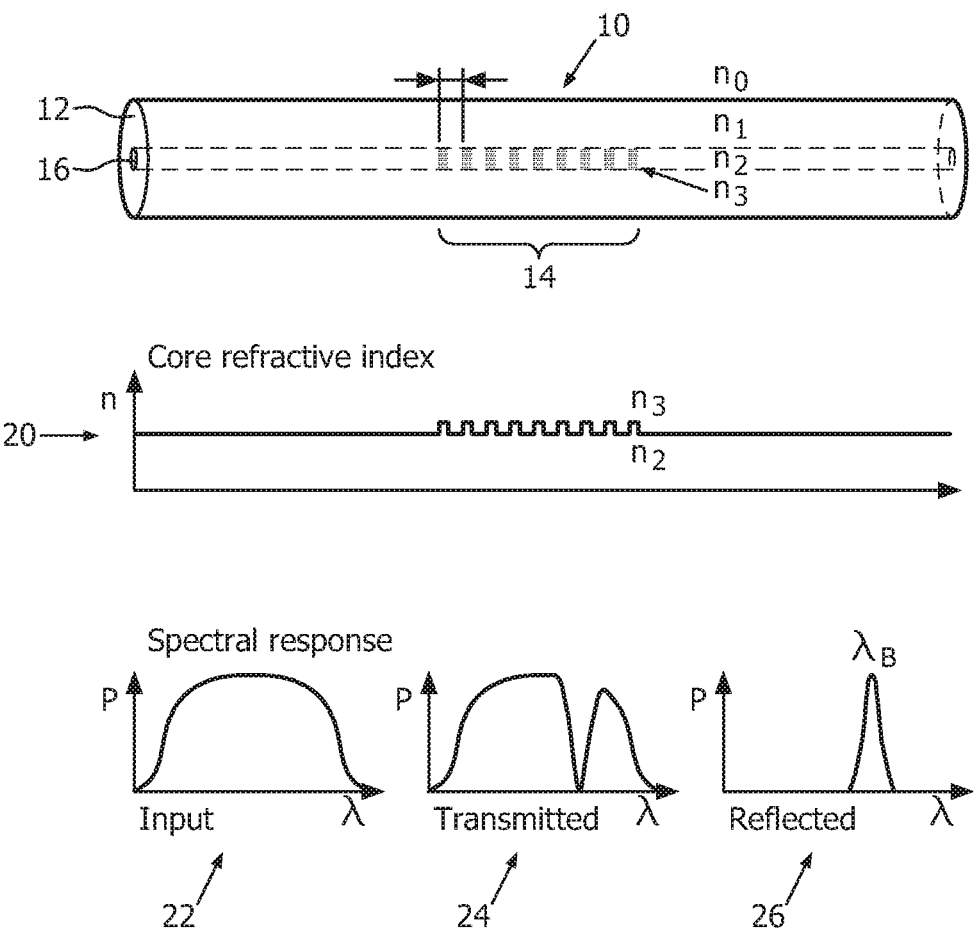
FIG. 1 shows an optical fiber including a Fiber Bragg Grating (FBG), a plot of index of refraction versus distance and spectral response due to the FBG.

The present disclosure describes an apparatus and method for real-time, markerless (no external markers are needed on a patient) tracking of a tip of a medical device, for example, a bronchoscope. Sensors, such as Fiber Bragg Gratings (FBGs) are integrated within a flexible insert that can be positioned within an instrument channel of the device. A system may include: (1) a bronchoscope or other instrument having at least one instrument channel, a light source, and an optical system for acquiring images (e.g., a CCD camera at the tip or a fiber bundle), (2) at least one optical fiber containing a plurality of FBG's to monitor, in a spatially distributed fashion, deflection or bending of the optical fiber, (3) an optical console that delivers light to the FBGs and receives light from them, with a corresponding shape determination program which computes parameters related to the deflection of the optical fibers, and (4) a computer system with a 3D volume of the bronchial tree acquired from a pre-procedural scan, preferably with, e.g., a segmentation of a bronchial tree. The apparatus and method assist in orienting a physician or technician in navigating through branch points in a bronchial tree or other structure, make reaching a target more efficient, decrease the time required for a procedure and make it easier to assure that a biopsy is taken from a correct location.

In one illustrative embodiment, a system is provided for real-time, markerless tracking of the tip of a bronchoscope. The system preferably utilizes Fiber Bragg Gratings (FBGs) integrated within a flexible sheath or insert that can be inserted into an instrument channel of the bronchoscope. One, two, three or more fibers may include integrated FBGs that can be utilized in conjunction with each other to track 3D shapes of the fibers in real-time.

It should be understood that the present invention will be described in terms of medical instruments; however, the teachings of the present invention are much broader and are applicable to any instruments employed in tracking or analyzing complex biological or mechanical systems. In particular, the present principles are applicable to bronchoscopic procedures of the lung, as well as endoscopic procedures in other areas of the body such as the gastrointestinal tract, blood vessels, etc. The elements depicted in the FIGS. may be implemented in various combinations of hardware and software and provide functions which may be combined in a single element or multiple elements.

The functions of the various elements shown in the figures can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), and non-volatile storage.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams, state transition diagrams, pseudocode, and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable medium providing program code for use by or in connection with a computer or any instruction execution system. For the purposes of this description, a computer-usable or computer readable medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

Referring now to the drawings in which like numerals represent the same or similar elements and initially to FIG. 1, a Fiber Bragg grating (FBG) 10 is illustratively depicted. In a particularly useful embodiment, the FBG 10 includes a short segment of an optical fiber 12 that reflects particular wavelengths of light and transmits all others. This is achieved by adding a periodic variation 14 of the refractive index in a fiber core 16, which generates a wavelength-specific dielectric mirror. A plot 20 of core refractive index versus distance is illustratively shown.

A fiber Bragg grating 10 can therefore be used as an inline optical filter to block certain wavelengths, or as a wavelength-specific reflector. An input spectrum 22 and respective output spectrums 24 and 26 illustratively show a transmitted portion (spectrum 24) and a reflected portion (spectrum 26) of the input spectrum 22. The fundamental principle behind the operation of a fiber Bragg grating 10 is Fresnel reflection at each of the interfaces where the refractive index changes. For some wavelengths, the reflected light of the various periods is in phase so that constructive interference exists for reflection and consequently, destructive interference exists for transmission.

The Bragg wavelength is sensitive to strain as well as to temperature. This means that Bragg gratings can be used as sensing elements in fiber optical sensors. In a FBG sensor, the strain causes a shift in the Bragg wavelength, $\Delta\lambda_B$. The relative shift in the Bragg wavelength, $\Delta\lambda_B/\lambda_B$, due to an applied strain ($\varepsilon$) and a change in temperature ($\Delta T$) is approximately given by:

$$\frac{\delta\lambda_B}{\lambda_B} = C_s\varepsilon + C_T\Delta T$$

The coefficient $C_s$ is called the coefficient of strain and its magnitude is usually around $0.8\times10^{-6}/\mu\varepsilon$ or in absolute quantities about 1 pm/$\mu\varepsilon$). The coefficient $C_T$ describes the temperature sensitivity of the sensor; it is made up of the thermal expansion coefficient and the thermo-optic effect. Its value is around $7\times10^{-6}/K$ (or as an absolute quantity 13 pm/K). While FBGs are particularly suited for use in accordance with the present principles, other sensors may also be employed.

Figure 2:
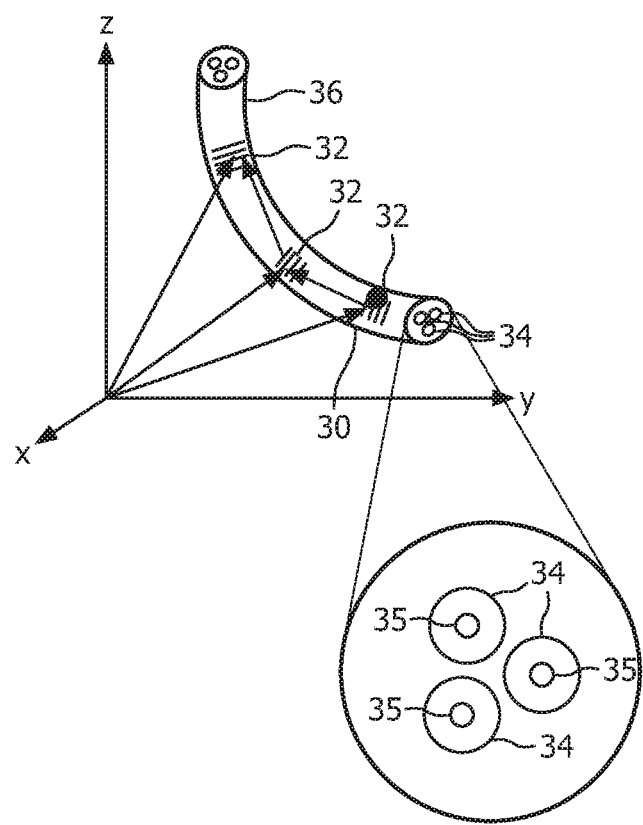
FIG. 2 shows a fiber triplet deflected in three-dimensional space.

Referring to FIG. 2, a fiber triplet 30 includes three fibers 34 and three FBGs 32. One advantage of employing the triplet 30 or a multiple fiber/FBG element is that various sensor elements can be distributed over the length of a fiber.

E.g., incorporating three cores with various sensors (gauges) along the length of the fiber embedded in a structure, the three dimensional form of such a structure can be precisely determined. Along a length of a fiber 34 at various positions, FBG sensors 32 are located. From the strain measurement of each FBG 32, the curvature of the structure 30 can be inferred at that position in three dimensional space (x, y, z). From the multitude of measured positions, the total three dimensional form is determined.

The fibers 34 are preferably potted in a flexible material, such as medical grade polymers (e.g., PEEK™). Fiber cores 35 are shown in an inset cross-sectional view. A sheath 36 surrounding the fibers may be constructed from medical grade polymers, silicone, or other suitable materials.

Figure 3:
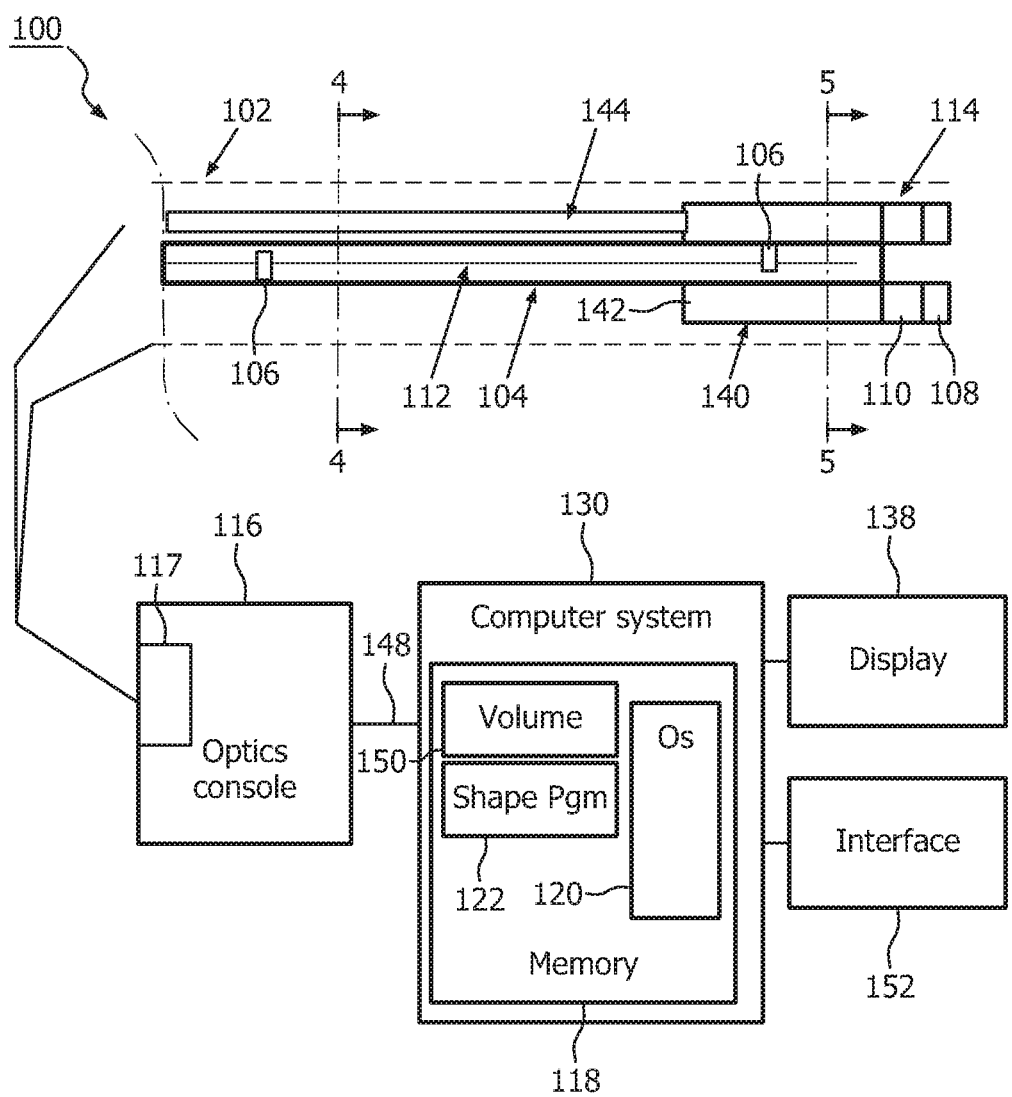
FIG. 3 is a diagram showing a cross-sectioned view of a scope with an apparatus therein including a flexible insert having an optical fiber with FBGs and a balloon for anchoring an end portion of the flexible insert.

Referring to FIG. 3, an apparatus or device 100 for real-time, markerless tracking of a tip of a medical instrument is illustratively depicted. Apparatus 100 is depicted in cross-section to render portions of the device visible. The device 100 may include a bronchoscope, a catheter, or similar device. Device 100 includes at least one instrument channel 102, which is configured to receive a sheath, insert or tube 104 having sensors 106 therein. A light source 108 may be provided on an end of the device 100 or may be located on a proximal end and transmit light through optical fibers 112. An optical system 114 includes components for acquiring images. These components 110 may include, e.g. a CCD camera 110 at the tip of the device 100, a fiber bundle, etc.). At least one optical fiber 112 is provided in the sheath 104 including one or more of sensors 106, which preferably include Fiber Bragg Gratings (FBGs) which monitor, in a spatially distributed fashion, the deflection or bending of the optical fiber 112.

The optical system 114 includes an optical console 116 that delivers light to the FBGs 106 and receives light from them. Console 116 may be connected to computer system 130 which includes memory storage 118 and operating system 120 with a corresponding shape determination program 122 which calculates parameters related to the deflection of the optical fibers 112. Computer system 130 (which may include console 116 or be an independent system) includes a 3D volume 150 of a bronchial tree acquired from a pre-procedural scan or other source, preferably with a segmentation (or map) of the bronchial tree for a bronchial procedure. While the example describes a bronchial tree, it is understood that other volumes, maps or images consistent with the application may be employed/provided. Console 116 may include an optical transreceiver 117 to transmit and receive optical signals or light and/or to retrieve live images from the distal end of the device 100. Camera 110 may be employed on the end of the scope to send video data back to the console 116. The video data from the camera 110 and/or from the optical fibers 112 may be correlated with a 3D volume or map 150 as will be described below.

Figure 3A:
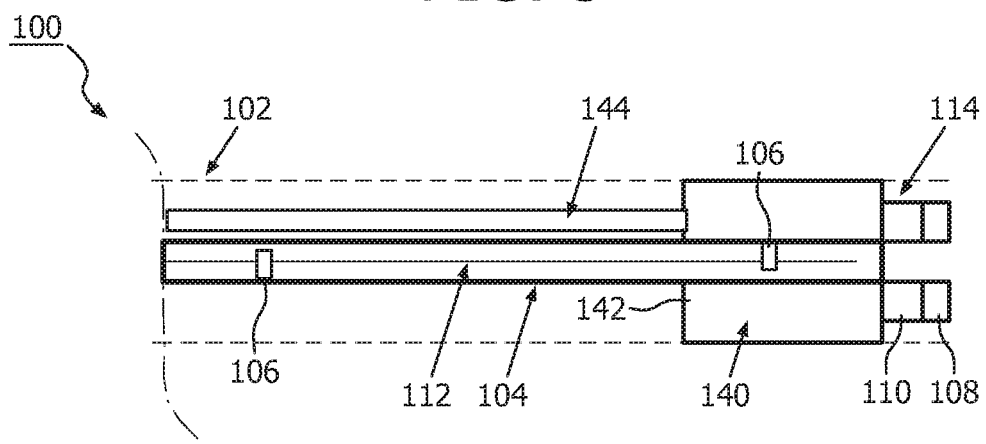
FIG. 3A is a diagram showing the cross-sectioned view of FIG. 3 with the balloon expanded for anchoring an end portion of the flexible insert.

In the depicted illustrative embodiment, the sheath 104 encloses the optical fibers 112 with the FBGs 106 within the instrument channel 102 of the bronchoscope. A fixing mechanism 140 is included and can be operated in at least two states. In an unexpanded state, a diameter of the channel 102 is sufficient to permit a physician/technician to insert the sheath 104 into the instrument channel 102 of the endoscope or device 100. In an expanded state, at least a part of the sheath 104 is in contact with the walls of the instrument channel 102, and therefore there is pressure exerted on the walls of the sheath 104 and the instrument channel 102. This expanded state resists slippage of the sheath 104 relative to the walls, preferably at the distal end of the bronchoscope or device 100. This provides that the bending of the fibers 112 closely approximates the bending of the bronchoscope 100. The expanded state may be realized by employing a balloon 142 and an inflation tube 144 to expand the balloon 142. FIG. 3 shows the balloon 142 in an unexpanded state, while FIG. 3A shows the balloon 142 in an expanded state.

There may be a data connection 148 between the optical console 116 and the computer system 130 containing a 3D volume 150 of the bronchial tree, or the console 116 may be included in the computer system 130. The computer system 130 produces a display 138 that shows the location of the bronchoscope tip determined by the shape determination program 122 (using measured strains from the sensors 106 (e.g., FBGs)), within the bronchial tree identified by the 3D volume 150.

Computer system 130 may include a user interface 152 for interacting with the console 116, the device 100 and/or the volume/map 150. The interface 152 may include a keyboard, a mouse, a touch screen system, etc.

Figure 4:
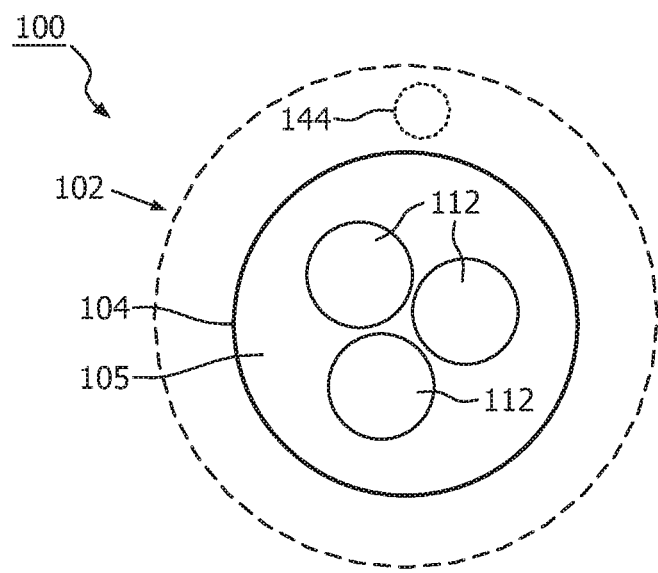
FIG. 4 is a cross-sectional view taken as section line 4-4 of FIG. 3.

Referring to FIG. 4, a cross-section taken at section lines 4-4 in FIG. 3 is depicted. Three optical fibers 112 including FBGs are arranged symmetrically within the flexible sheath 104 with a diameter that permits the sheath 104 to be inserted without resistance into the instrument channel of the endoscope or device 100. Flexible potting material 105 holds the fibers including the FBGs 106 in place relative to each other and relative to the sheath 104. By fixing the fibers in the potting material 105, predictable strain responses can be obtained.

Figure 5:
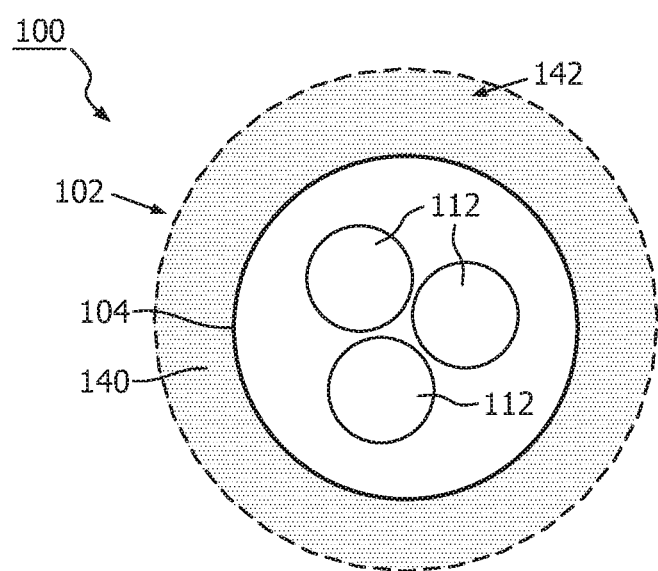
FIG. 5 is a cross-sectional view taken as section line 5-5 of FIG. 3.

Referring to FIG. 5, a cross-section taken at section lines 5-5 in FIG. 3 is depicted. At a tip of the bronchoscope or device 100, a torus-shaped balloon 142 is firmly attached to the flexible insert or sheath 104. The balloon 142 can be inflated and deflated by means of pressure delivered via a thin flexible tube 144 that extends towards the proximal end of the bronchoscope 100 outside the flexible sheath 104. In its deflated state, the balloon wall does not exert significant pressure on the inside wall of the instrument channel 102. In its inflated state, the balloon 142 exerts pressure on the inside wall of the instrument channel 102 so that there is significant friction that prevents the balloon/sheath combination from easily being withdrawn from the instrument channel 102.

Figure 6:
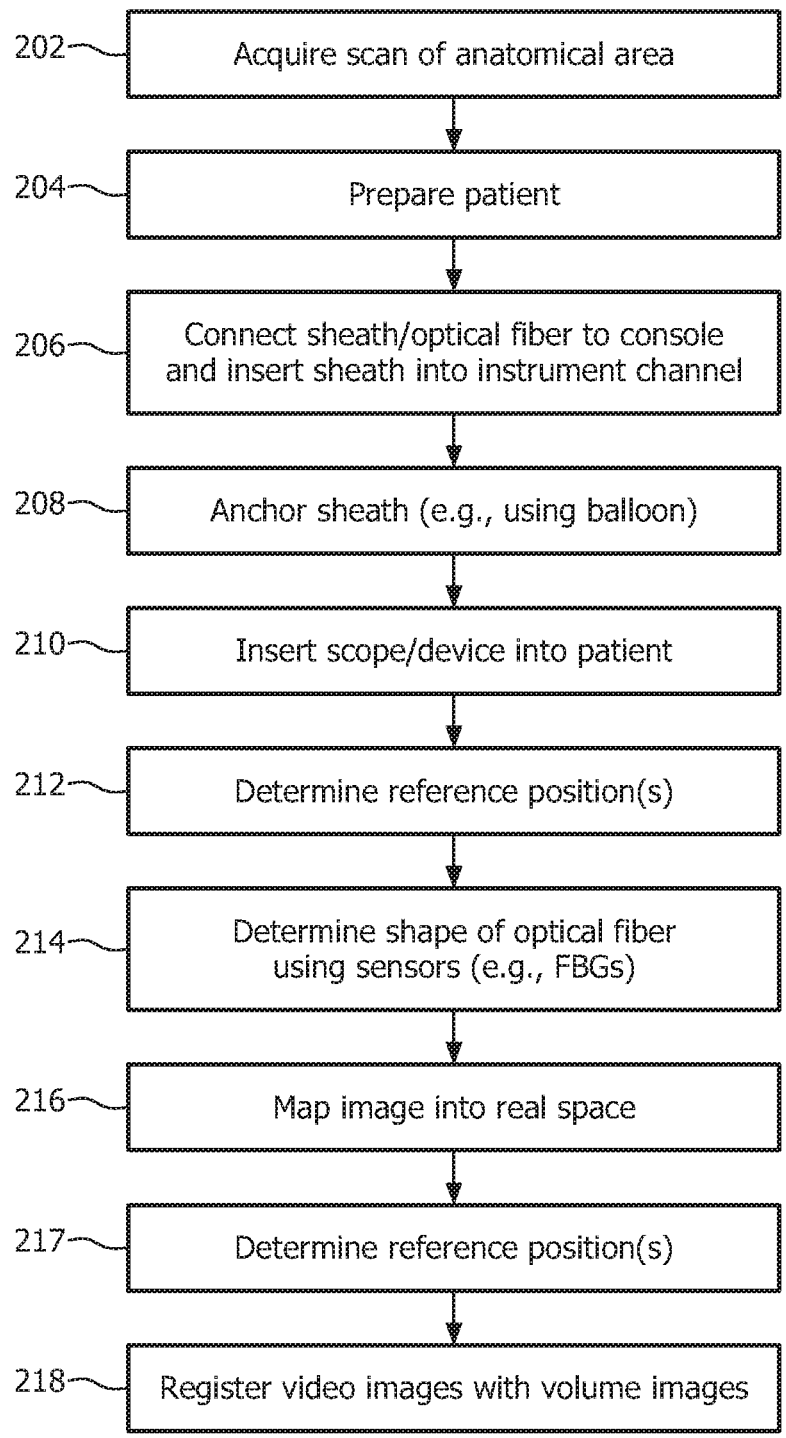
FIG. 6 is a flow diagram showing an illustrative procedure for tracking a bronchoscope within a body in accordance with one embodiment.

Referring to FIG. 6, a method for employing the device (100) is illustratively shown in accordance with one embodiment. The sheath (104)/balloon (142) combination may be employed as follows. In block 202, a pre-procedural scan (e.g., CT) is acquired for the anatomical area to be examined (subject of the procedure). In block 204, the patient is prepared for a bronchoscopy or other procedure. In block 206, a sheath (104) is connected to the optical console (116) and inserted into instrument channel (140) of the bronchoscope with the balloon (142) in a deflated state. The sheath is inserted into an instrument channel. The sheath includes an optical fiber and a plurality of distributed sensors integrated with the optical fiber (or fibers).

In block 208, the sheath is anchored within the instrument channel. This may include employing a balloon (142). The balloon is inflated to secure the sheath (104) within the bronchoscope or device (100). Pressure applied to the optical fiber by the balloon at a tip of the instrument channel produces a strain in the optical fiber to locate the tip of the instrument channel inside a body. The strain due to the balloon on the fiber will provide an indication of where the tip is located.

In block 210, the scope/device (e.g., bronchoscope) is inserted into the patient. In block 212, a reference position is determined within a patient using the pre-procedural volume of the patient. At a particular location such as the entrance to the bronchial tree, the physician indicates to the computer system (130) that a particular location corresponds to the reference location and annotates the corresponding location on the pre-procedural image volume. In block 214, a shape of the optical fiber is determined using the sensors, and the shape is correlated with the pre-procedural volume to provide a location of the portion of the medical device. As the bronchoscope is inserted further within the bronchial tree, the shape of the bronchoscope as determined by the shape determination program (122) is correlated with the pre-procedural volume, preferably with the segmented bronchial tree, by the computer system (130). The shape determination program receives as input optical measurements from the Fiber Bragg Gratings and provides as output an estimate of the three-dimensional shape of the flexible structure in which the FBGs are embedded. The program may involve a two step process, where optical measurements are first converted to strain measurements, the strain measurements are then processed in combination to yield the estimate of the three dimensional shape of the flexible structure. This correlation would reveal the location of the tip of the bronchoscope within the bronchial tree; the location would be displayed in real-time, guiding the physician to the tissue target.

In block 216, video data may be acquired for reconstructing an image of the body (from inside). As the bronchoscope video data are acquired, rapid algorithms for 3D reconstruction from image shading cues can be used to obtain surface maps within the bronchoscope field of view. In block 217, the image is mapped back into real space using shape information derived from the sensors, thereby providing a map between image pixels in camera space and the optical shape sensing reference coordinate system. Each of the 3D surfaces in the video images can be mapped back into real 3D space by using the bronchoscope camera position (e.g., at the end of the scope 100) and orientation information derived from the FBG data in combination with a calibration matrix which maps image pixels in camera space back into the optical shape sensing reference coordinate system.

Video processing and image comparisons may be performed using programs which search for and compare images to identify a best match. In this way, sufficient and redundant clues are provided to identify a position and orientation of at least the distal end of the scope in real-time during a procedure.

In block 218, reconstructed images can be dynamically registered using pre-procedural volumetric imaging to further improve registration quality and navigation accuracy. The reconstructed 3D airway surfaces from the FBG-enabled bronchoscopy system can be registered with pre-procedural volumetric imaging from CT or magnetic resonance (MR) to further improve registration and navigation accuracy. For example, the pre-procedural volumetric images could be segmented to derive the 3D contours of the bronchi, which in turn could be utilized as prior information to improve the accuracy of the map between image pixels in camera space and the optical shape sensing reference coordinate system. As an example, the 3D contours of the bronchi estimated from pre-procedural volumetric images could be utilized to determine constraints on the spatial position of the bronchoscope.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for systems and methods for a flexible instrument channel insert for a scope with real-time position tracking (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A method for tracking of a medical device, comprising:
  inserting a sheath into an instrument channel of the medical device, the sheath including an optical fiber and a plurality of distributed fiber Bragg sensors integrated with the optical fiber;
  inflating a balloon disposed around a tip of the sheath to anchor the sheath within the instrument channel and to cause strain on fiber Bragg sensors of the plurality of distributed fiber Bragg sensors disposed adjacent the tip of the sheath;
  acquiring video images in camera space from a camera disposed at the tip of the sheath;
  determining a reference position within a patient in real space using a pre-procedural volume image of the patient;
  using the fiber Bragg sensors, determining a shape of the optical fiber and a location of the tip of the sheath from gain strain caused by inflating the balloon;
  correlating the shape of the optical fiber and the location of the tip of the sheath with the reference position determined from the pre-procedural volume image to provide a location of the camera; and
  mapping the video images into real space using the location of the camera, the shape of the optical-fiber and the location of the tip of the sheath.

2. The method recited in claim 1, wherein the balloon includes a torus shape such that the sheath fits within the tows shape and an outside of the torus shape contacts an inside of the instrument channel and an inside of the torus shape contacts an outside of the sheath.

3. The method recited in claim 1, wherein the medical device is a bronchoscope and the pre-procedural volume image comprises a segmented bronchial tree.

4. An apparatus for determining a position of a medical device, comprising:
  a sheath configured to fit within an instrument channel of a bronchoscope;
  at least one optical fiber disposed within the sheath;
  a plurality of fiber Bragg grating sensors in optical communication with the at least one optical fiber, the fiber Bragg grating sensors being configured to shift wavelengths of light in the at least one optical fiber in response to strains on the fiber Bragg grating sensors caused by deflections and bending in the at least one optical fiber;

a camera disposed at a tip of the sheath;

a toroidal balloon disposed around the sheath at the tip of the sheath and having a deflated state and an inflated state, wherein in the deflated state, the toroidal balloon is sized to fit within the instrument channel and, in the inflated state, the toroidal balloon is configured to (i) fixedly engage the instrument channel and the sheath, and (ii) cause strain on fiber Bragg grating sensors of the plurality of fiber Bra grating sensors that are adjacent the tip of the sheath and the camera, the strain on the fiber Bragg grating sensors adjacent the tip of sheath and the camera shifting the wavelengths of the light in the at least one optical fiber adjacent the tip of the sheath;

an optical interface connected between the at least one optical fiber and a computer system configured to:

determine a shape of the at least one optical fiber and a location of the tip of the sheath from the shifts in the wavelengths of light in the at least one optical fiber;

based on the determined shape of the at least one optical fiber and the determined location of the tip, map a position of the bronchoscope to a depiction of a 3D bronchial tree retrieved from a computer memory; and control a display to display one or more of the location of the tip, the bronchial tree with the mapped position of the bronchoscope and the tip, and video images from the camera.

5. The apparatus recited in claim 4, wherein the at least one optical fiber includes a fiber triplet.

6. A method for tracking a medical scope with images, the method comprising:

acquiring a preprocedural diagnostic image of an anatomical area to be examined with the medical scope;

inserting an assembly into the instrument channel, the assembly including a sheath, an optical fiber, a plurality of fiber Bragg gratings optically connected with the optical fiber such that strains on the fiber Bragg gratings change wavelengths of light in the optical fiber, a toroidal balloon disposed around a tip of the sheath, the toroidal balloon having a deflated state for insertion into the instrument channel and an inflated state in which the toroidal balloon fixes the assembly in the instrument channel and applies strain to fiber Bragg gratings of the plurality of fiber Bragg gratings disposed at the tip of the sheath, and a camera disposed at the tip of the sheath;

inflating the balloon to secure the sheath within the instrument channel and apply pressure to the optical fiber and the fiber Bragg gratings to cause strain at the tip of the sheath, which in turn causes changes in the wavelengths of the light that are indicative of the location of the tip of the sheath;

inserting the medical scope into a patient;

selecting a reference position in the preprocedural diagnostic image;

determining a shape of the optical fiber based on the changes in the wavelengths of the light in the optical fiber and determining a location of the tip of the sheath relative to the selected reference position in the preprocedural diagnostic image based on the changes in the wavelengths of the light in the optical fiber;

acquiring a series of video images from the camera, the video images depicting tubular structures through which the medical scope is moved into real space;

from the shape of the optical fiber and the location of the tip of the sheath, mapping the series of video images of surfaces of tubular structures through which the medical scope is moved into real space; and dynamically registering the preprocedural diagnostic image with the video images to reconstruct 3D passage surfaces to derive 3D contours of the passages.

7. The method recited in claim 6 wherein the medical scope is a bronchoscope, the preprocedural diagnostic volume image depicts a bronchial tree, and the tip of the bronchoscope is moved through the bronchi to perform a real-time examination thereof.

8. The method recited in claim 6, wherein the dynamic registering includes:

segmenting the preprocedural diagnostic volumetric image to derive 3D contours of the bronchi;

utilizing the derived 3D contours as prior information to improve an accuracy of mapping between image pixels in camera space and real space.

* * * * *